United States Patent [19]

McDevitt

[11] 4,084,441

[45] Apr. 18, 1978

[54] DEVICE FOR OBTAINING A SAMPLE OF MOLTEN MATERIAL AND DEOXIDIZING ELEMENT FOR USE THEREWITH

[75] Inventor: Robert F. McDevitt, Ogden Dunes, Ind.

[73] Assignee: Charles S. Penfold, Fort Wayne, Ind.

[21] Appl. No.: 792,340

[22] Filed: Apr. 29, 1977

Related U.S. Application Data

[62] Division of Ser. No. 720,697, Sep. 7, 1976.

[51] Int. Cl.² ............................................... G01N 1/12
[52] U.S. Cl. .............................................. 73/425.4 R
[58] Field of Search .................... 73/425.4 R, DIG. 9; 164/4

[56] References Cited

U.S. PATENT DOCUMENTS

| 3,646,816 | 3/1972 | Hance | 73/425.4 R |
| 3,791,219 | 2/1974 | Falk | 73/425.4 R |
| 3,859,857 | 1/1975 | Falk | 73/425.4 R |

Primary Examiner—S. Clement Swisher

[57] ABSTRACT

The invention involves a device for obtaining a sample of molten material, and a particular form of a means for deoxidizing or conditioning this material. The deoxidizer is in the form of a generally tubular element which can be deformed for insertion into the inlet tube of a molten metal samoler so that it is held by the resilient force of the element.

12 Claims, 12 Drawing Figures

DEVICE FOR OBTAINING A SAMPLE OF MOLTEN MATERIAL AND DEOXIDIZING ELEMENT FOR USE THEREWITH

The subject application is a Division of my parent application Ser. No. 720,697 filed Sept. 7, 1976.

BRIEF SUMMARY OF THE INVENTION

More particularly, the purpose of the invention is to provide a safe and simple method whereby a cast sample for example, may be obtained from a flowing metal stream when molten metal is being transferred by pouring from one type vessel to another. The cast sample may consist of a disc with one or more smaller cast extensions attached to the disc. The size and shape of the casting is designed to provide a precision sample, requiring a minimum of preparation, that meets laboratory testing procedures. The disc may be used directly for spectographic analysis or can be drilled to provide a sample for wet chemical analysis. In addition, the sample may be sawed and polished for use in metallographic study of grain structure, cleanliness, etc. The smaller cast extensions are of precision dimensions with indexed separation points to permit detaching a sample of precise weight, minimizing preparation. These smaller samples are suited for analysis of such elements as sulfur or carbon.

The entire sample (disc and extension) can be cast in a two piece mold assembly made of a material with optimum cooling venting and dimensional characteristics. This sample is representative of the material being tested and can be used for either chemical analysis or metallographic examinations.

DESCRIPTION OF THE TESTING PROCEDURE

In the processing of metals in the molten state it is necessary to obtain a sample representative of the parent material, at various stages in the processing, for the evaluation of either its chemical composition or metallographic structure.

The device or sampler embodying the subject invention is preferably designed to obtain a quick chilled sample from the flowing metal as it is transferred by pouring from one type vessel to another. It is primarily designed to be used where molten steel is poured from a teeming ladle into a mold. The molten steel is teemed through a nozzle in the bottom of the ladle, and the resulting stream is controlled through use of a mechanical, electro, or hydraulic valve arrangement. The diameter of the stream can be from ¾ to 3½ inches depending on the rate of flow desired.

The device also has application in the continuous casting process during transfer of molten metal from ladle to tundish to mold under controlled condition. This device has further application in any area or with any molten metal where the molten metal is transferred from one vessel to another under controlled conditions.

For many years the typical method of sampling molten metal in the steel industry was to use what was defined as a spoon. The spoon consisted of a deep bowl type ladle or sampler attached to the end of a long handle and made of either cast or forged steel. The spoon varied in size and has a lip to facilitate pouring. In practice the pouring stream was controlled to a slow or partial stream and the spoon was then dipped into the stream of metal to obtain the sample. The spoon was usually tipped into either the right or left side of the stream, whichever was most convenient, and partially filled with molten metal. The molten metal content of the spoon was then poured into a small test mold positioned on the platform. The casting from this mold provided a sample 4 to 8 inches long, tapered, and 1 to 2 inches square in cross-section. The sample could be sawed or drilled in the laboratory to provide samples for wet chemistry analysis, spectrographic analysis or metallographic evaluations. The samples obtained as described above are used to represent a portion of the metal in the teeming ladle at given intervals in the pouring process.

This conventional method of sampling is not only wasteful from the standpoint of time and material but also exposes the molten metal to atmospheric oxygen which can cause variations in the chemical content of the sample. The degree of the chemical variation is dependent on the grade of steel as well as the techniques of the individual doing the sampling. The effect is most pronounced with the elements of carbon and manganese with varying effects on other elements. Although the steel industry has been aware of the phenomenon and does make corrections; much could be gained by minimizing this condition. Other disadvantages of this conventional method are the need to arrest the stream and the extreme safety hazards involved with taking a sample when the molten metal stream cannot be controlled.

Advantages of the invention or inventions over the spoon technique are:
1. Minimum exposure of the sample to atmospheric oxygen.
2. Simplified sampling technique eliminating the heavy spoon and repouring technique.
3. Elimination of the need to arrest the molten metal stream flow.
4. Precision cast samples with a quick chill and tailored for minimum preparation.
5. Representative and reproducible results at a minimum of expense.
6. Safe procedure in obtaining samples.

In view of the foregoing, one of the important objects of the invention is to provide an elongated device for obtaining a sample of a liquid, such as molten metal, which comprises, among other things, a pair of half sections forming a chamber, tubular means which has an inner extremity communicatively connected to the chamber and an outer extremity provided with an entrance for initially receiving molten metal for flow into the chamber, means at one extremity of the device for holding the sections together, and means at its opposite extremity for holding the sections and tubular means assembled, and wherein one or both of these holding means may serve to facilitate disassembly of the sections. More particularly in this respect, one of the holding means for the sections comprises clip means, and an appendage held in place by this clip means may be utilized for identificating purposes and effect release of the clip means, and the means for holding the sections and tubular means may be operated to facilitate disassembly for these components.

A significant object of the invention is to provide a device of the character described above in which each section includes a relatively large head portion provided with a recess, and an extended portion having a center groove therein so that when the sections are correctly assembled the recesses will form a primary chamber for receiving a sample of molten metal and the grooved extensions will form a tubular formation communicating with the chamber, an entrance tube is disposed in the tubular formation and a unique generally split tubular means is frictionally held in the tube for conditioning the molten metal as it flows into the chamber.

Additional objects and advantages of the invention reside in providing a device which is safe and efficient to use, durable and comprised of components which can be economically manufactured and assembled on a production basis.

Other objects and advantages will become apparent after the description hereinafter set forth is considered in conjunction with the drawings annexed hereto.

DESCRIPTION OF THE PREFERRED EMBODIMENTS

Figure 1:
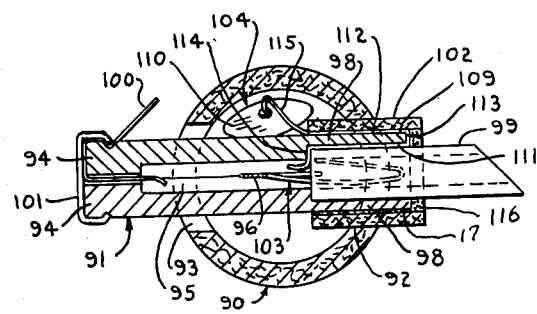
FIG. 1 is a sectional view of a connector device operatively connected thereto.
Figure 2:
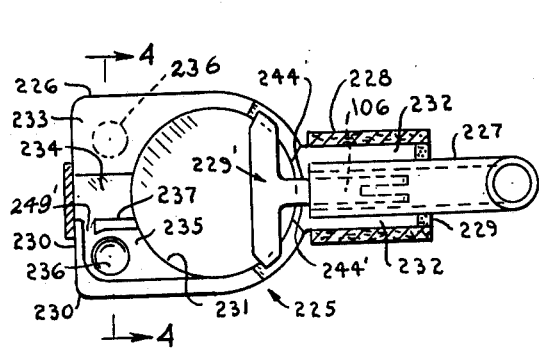
FIG. 2 is a longitudinal section taken substantially on line 2—2 of FIG. 3 of a modified device.
Figure 7:
FIG. 7 is a perspective view of a modified form of a deoxidizing element which may be utilized in a mode different from that of the element shown in FIG. 6.

The claims in the subject application are primarily directed to the means or deoxidizer shown in FIG. 7 and its operative relationship to devices, such as those depicted in FIGS. 1 and 2.

FIG. 1 discloses a form of a tubular connector generally designated 90 and modified device generally designated 91. The connector is provided with a pair of aligned round side openings 92 and 93 of different diameters disposed on a line transverse to the longitudinal axis of the connector.

Figures 4, 5:
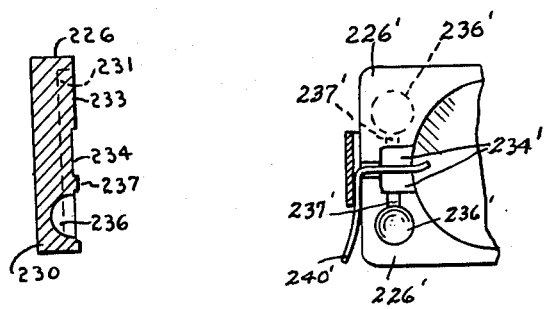
FIG. 4 is a transverse section taken substantially on line 4—4 of FIG. 2.
FIG. 5 is a partial inside view of one of a pair of half sections for use in a modified device.
Figure 12:
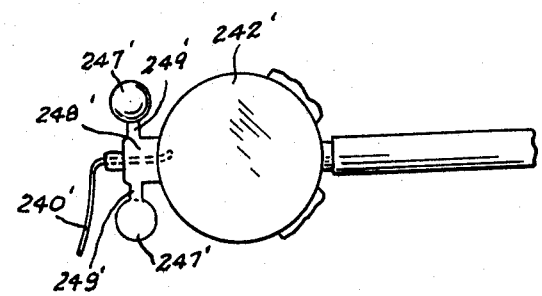
FIG. 12 is a sample obtained by utilizing the half sections depicted in FIG. 5.

The device 91 is quite similar to the device shown in FIG. 12 of applicant's parent application and comprises a pair of recessed half sections 94 constructed to provide a chamber 95 and side vents 96 like the vent 18 shown in FIGS. 4 and 12 of that application. These half sections also include channel portions 98 which form a tubular formation for receiving an inner extremity of a tubular means 99. The device also includes an appendage 100, clip means 101, and a sleeve 102, including a metal deoxidizing element generally designated 103 and what may be termed a trigger assembly generally designated 104.

Figure 6:
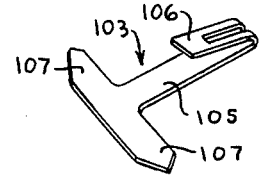
FIG. 6 is a perspective view of a deoxidizing element which may be utilized in conjunction with the devices shown in FIGS. 1 and 2.

The deoxidizing element 103 may be designed and constructed as desired but is preferably generally T-shaped or articulated as exemplified in FIG. 6 and includes a stem 105 having a slotted continuation 106 bent back at an acute angle over the stem and a pair of opposed portions 107 constituting the cross of the T. This element is secured in place by locating remote ends of the portions 107 in the vents and the stem 105 and its continuation 106 in the tubular means 99 so as to insure the inflow of metal will be thoroughly subjected to conditioning by the deoxidizing means both in the tubular means and chamber. The continuation 106 due to its slotted character serves to expedite melting thereof and conditioning of the metal. The free ends of the portions 107 of the element are preferably bevelled or pointed to some extent as shown in FIGS. 2 and 6 for disposition in side openings or vents 96 formed by the notches in the head portions so that some metal may flow outwardly through the vents to provide laterally extending arcuate portions 108 of a sample as depicted in FIG. 9, which will be described subsequently.

The trigger assembly generally designated 104 is unique and preferably includes a generally U-shaped metal member 109 and a disc-like handle 110. The member has a leg 111 located between one of the portions 98 of the head sections and the tubular means 99 and a leg portion 112 between the portion 98 and the sleeve 102, a bridge portion 113 engaging an end of the portion 98, an offset inner end portion 114 extending into the chamber 95 and an outer offset end 115 to which is connected the handle 110 or a tag. This trigger assembly affords a setup whereby after a sample has been obtained, the handle or tag can be pulled in the appropriate direction or directions whereby to assist in separating the sleeve 102 from the half sections and tubular means. It should be noted that means, such as cement or a washer 116 of pasteboard is preferably secured in the outer end of the sleeve and about the tubular means to provide a seal therebetween. It should also be noted that the side opening 92 above referred to, has a diameter to facilitate entry of the sleeve 102 of the device and that the opening 93 is larger than the opening 92 and accomodates the head or larger extremity of the device. It should be further noted that the device may be rotated about its axis relative to the connector to any position desired by an operator to facilitate entry of the tubular means into the molten metal. The tubular means 99 may be secured in place in the tubular formation formed by the channel portions 98 by the cement or as alluded to above.

Figure 3:
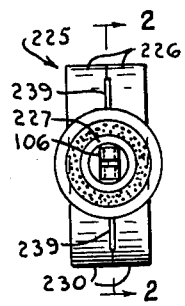
FIG. 3 is one end view of the device of FIG. 2.
Figure 9:
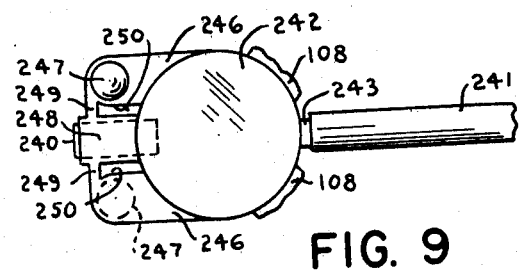
FIG. 9 is a top view of sample of molten metal obtained by using the device shown in FIG. 2.
Figure 10:
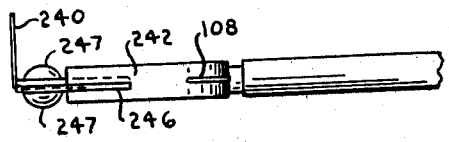
FIG. 10 is a side view of the sample shown in FIG. 9.
Figure 11:
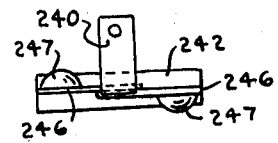
FIG. 11 is one end view of the sample depicted in FIGS. 9 and 10.

FIGS. 2, 4 and 3 disclose a modified device generally designated 225 whereby a sample or portions may be obtained as shown in FIGS. 9, 10 and 11 and one or more portions thereof may be removed as depicted in FIG. 25 of said parent application. The device 225 is substantially the same as the device 90 except that it includes half sections generally designated 226 which embody different and unique structural advantages. The device does include a tubular means 227, sleeve 228, washer or cement 229 and the deoxidizing element 229' like 103.

As to the half sections 226, each comprises a generally rectangular head portion 230 provided with a round recess 231, channel portions 232 (one shown) and a solid outer end portion 233 provided with an axially extending rectangular slot 234, a relatively shallow recess 235 which is provided with a substantially semi-spherical secondary chamber or pocket 236, a longitudinally extending rib 237 constituting a side wall of the slot 234. When the sections are correctly assembled, the recesses 231 define: a primary chamber for receiving molten metal from the tubular means 227, the side notches, openings or vents 239 for the portions of the deoxidizing element 229', the axial slots 234 an opening which receives a portion of an appendage 240, as shown in FIG. 9, the shallow recesses 235 on the opposite sides of the longitudinal axis of the device respectively provide relatively broad passages through which metal may flow into the opening formed by the axial notches 234. Otherwise expressed, metal may flow from the primary chamber into the secondary chambers 236 and vents 239 so that when the metal solidifies a sample or portions will be obtained as shown in FIGS. 9, 10 and 11. An appendage 240, like the appendage 31, is preferably disposed in the axial opening for imbedment in metal and clip means is also employed for detachably holding head portions of the sections together. The size of the secondary chambers 236 are preferably predetermined so that, for example, portions obtained will each weigh one gram. However, it is to be understood that these secondary chambers may be in different sizes and shapes.

More particularly, the sample or portions illustrated in FIGS. 9, 10 and 11 include a cylindrical stem portion 241 formed in the tubular means 227, a round head portion 242 of substantially uniform thickness which may correspond to the crossdimension of the stem portion and an intermediate restricted portion 243 formed in a passage 244 of the sections. The material defining the passage constitutes an abutment 244'. Attached to the head 242 are circumferentially spaced relatively thin outwardly extending radial portions 108 formed in the side openings or vents 239, a pair of parallel relatively thin portions 246 of uniform thickness which are located on opposite sides of and in parallel relation to the longitudinal axis of the stem. The portions 246 are formed in the recesses 235 and extend in a direction opposite to that of the stem and the outer extremity of each of the portions 246 includes hemispherical portions 247 formed in the secondary chambers 236, each of which is intended to weigh, for example, one gram. It will be noted an axially extending portion 248 is formed in the opening formed by the slots 234 and that the portion 248 is joined to the outer extremities of the parallel portions 246 by portions 249 formed in passages 249'. It should also be noted that the head portion, parallel portions, axial portion and transverse portions define openings 250.

Figure 8:
FIG. 8 is a transverse section showing the element of FIG. 7 held in a tube of the device of FIG. 2.

If found desirable, a deoxidizing element 251, as illustrated in FIG. 7, may be utilized in lieu of the element 103; for disposition in the tubular means 227 as depicted in FIG. 8. The element 251 is preferably resiliently flexible and in the form of a strip of aluminum which is rolled generally into a generally cylindrical shape and is provided with an internal portion 252. The outside diameter of the element is preferably slightly larger than the inside diameter of the tubular means 227 so the element when manually inserted into the tubular means will be automatically held in position. The element 251 is preferably adapted for disposition in the tubular means 227 and against the abutments 244' in lieu of utilizing the element 103.

FIG. 5 illustrates a partial view of portions of a pair of half sections 226' similar to the half sections in FIG. 17 which are respectively provided with round recesses for forming a primary chamber for receiving molten metal so that a head portion 242' of a sample also having a stem is obtained as depicted in FIG. 12. The half sections are also provided with end notches 234' which define a pocket for forming a portion 248' of the sample and with adjacent notches which define an axial opening through which a length of wire 240' extends. This wire also extends into the chamber and is preferably held in place by a clip means as clearly shown. This wire is held to the sample when the latter is formed as shown in FIG. 12. The outer end of the wire may be provided with a tag for identifying the sample.

The half sections are further provided with semispherical recesses 236' which respectively provide sample portions 247' as shown in FIG. 12. These recesses constitute secondary chambers and the molten metal flows thereto through transverse passages 237' which communicatively connect the pocket formed by the notches 234' with the secondary chambers to obtain the sample portions 247', just referred to, which are joined to the portion 248' by connecting portions 249' formed in the transverse passages 237'. The portions 247' are preferably of a size to weight substantially one gram each to facilitate analysis thereof.

It is to be understood that the half sections or receiving means can be fabricated from any material initially for the purpose, such as ceramic material, solid cast or forged metals such as copper, iron and steel, stamped from sheet metal stock. Sintered powdered metal is preferred because of certain unique characteristics it possesses. A properly designed powdered metal mold with adequate venting will form a fast chilled sample with a minimum of chemical segregation, optimum metalographic structure and precision dimensions for ease of preparation and analysis.

Elucidating further with respect to the use of the device in obtaining a sample, the sampling device is attached to the end of the lance or wand so that the feed tube of the device is perpendicular to the axis of the pole as disclosed in said parent application. The individual taking the sample grasps the handle, faces the stream of molten metal, and holding the sample such that the feed tube of the device is near and parallel to the flow of the metal stream, twists the assembly so the open end of the feed tube is injected into the flow of the molten metal. The opening of the tube should be held at an angle to permit an unrestricted flow of the metal down the inside of the tube into the interior of the device. The open end of the tube is inserted just inside the outer surface of the stream to utilize the full volumetric capacity of the feed tube and minimize exposure of the incoming metal to the atmosphere.

As the sampling time using the invention so short, the sample size small and the mold enclosed, exposure to the atmosphere is greatly reduced, therefore reaction of the molten metal with oxygen is limited. Another important factor is the rapid transformation is accelerated by the mold design and the material employed. Rapid solidification minimizes chemical segregation and promotes a uniform structure.

It is theorized that when a molten metal sample is taken using powdered metal molds the sample is transformed quickly from the liquid to solid state by the combined action of the emissivity of the surface which allows the sintered iron mold to absorb the heat rapidly and the good conductivity of the iron allows the heat to transfer throughout the mass of the mold by conduction and convection. The good radiation characteristics of the outer surface allows for dissipation of the heat to the atmosphere. The quick chill effect of the mold design of the device coupled with its venting characteristics have permitted the design to incorporate the use of small extensions attached to the primary disc. These extensions are used primarily for the analysis of carbon and sulfur and their globular shape allows uniform cooling and solidification of the molten metal with a minimum of chemical segregation. Analysis of the elements from these samples may compare more favorably with analysis of drillings obtained from the primary disc and also with analysis obtained from product checks and possibly samples severed from glass enclosed pins which may cool differentially and have a tendency to segregate chemically.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. A device for obtaining a sample of liquid from a stream thereof, said device comprising a pair of elongated half sections, each of said sections being provided with an enlarged portion provided with a recess and a smaller channel portion, means securing said enlarged portions together and means securing said channel portions together whereby said recesses and said channel portions respectively form a chamber and an elongated opening, a tube having an inner extremity secured in said opening and an outer extremity provided with an entrance for a liquid for flow into said chamber via said tube, and substantially split tubular means secured in said tube for conditioning the liquid as it flows therethrough.

2. The device defined in claim 1, in which said first mentioned means has leg portions which straddle said enlarged portions and said means securing said channel portions comprises a sleeve which surrounds said channel portions and assists in holding said tube in said opening.

3. A device for obtaining a sample of liquid from a supply thereof, said device comprising wall structure forming a chamber and an elongated opening communicating with said chamber, a tube having an inner extremity disposed in relation to said opening and an outer extremity provided with an entrance for entry of a liquid into the tube for flow into said chamber, and substantially tubular expansible and contractible deoxidizing means disposed in said tube.

4. A device for obtaining a sample of liquid from a supply thereof, said device including a subassembly comprising a pair of half sections, each of said sections comprising a head provided with a recess and a channel extension and resiliently flexible clip means for engaging and securing said heads whereby the recesses and extensions respectively form a chamber and an opening, tubular means having an inner extremity secured in relation to said opening and an outer extremity provided with an entrance whereby liquid may be caused to flow through said tubular means into said chamber, and split tubular means disposed in said tubular means for conditioning the liquid as it flow therethrough.

5. A structure for use as a means of a device for obtaining a sample of molten material from a supply thereof, said structure comprising walls forming an enlargement provided with internal surfaces forming a primary chamber having an entrance, split tubular means having an inner flange, secured in said entrance for conditioning the molten material, said enlargement also being provided with internal surfaces forming a secondary chamber whereby the molten material entering said entrance will flow outwardly therefrom successively into said primary and secondary chambers for eventual solidification against the internal surfaces thereof whereby to form a sample substantially within the confines of said chambers which has a large portion and a smaller portion of a predetermined size extending from said large portion, and said enlargement being provided with means integral therewith for substantially preventing the outflow of molten material from said secondary chamber.

6. In combination: a refractory tubular structure for receiving a molten material, and meltable means comprising a split tubular element of an expansible and contractible character frictionally held in said tubular structure through which such a material will flow for melting said means for conditioning the material.

7. In combination: a refractory tubular structure for receiving a molten material, and conditioning means disposed in said tubular structure, said conditioning means being generally in the form of a split tubular element having an external wall frictionally engaging an inner surface of said tubular structure and a portion extending into said element whereby molten material may be caused to flow through said means and about said extending portion whereby to facilitate melting and mixing thereof into such a material.

8. A device for obtaining a sample of molten material comprising wall structure forming a chamber and a refractory tube communicatively connected to said chamber, means for holding said structure and tube assembled, means for conditioning the molten material when it flows through said tube into said chamber, said conditioning means comprising a split tubular element having an inner longitudinally extending wall portion dividing its interior into a pair of passages through which the material may flow whereby to facilitate melting of this element for mixing with such material for the purpose described.

9. The device defined in claim 8, in which said element is generally of an expansible and contractible character and has an outside cross-dimension which is slightly greater than an inside cross-dimension of said tube whereby when said element is manually inserted into said tube to a predetermined position it will automatically stay in this position.

10. The device defined in claim 8, in which said element is constructed of a material which serves to deoxidize the molten material.

11. An element for the purpose described comprising a substantially split cylindrical tubular element which is contractible and expansible.

12. A deoxidizing means adapted for use in a device for obtaining a sample of molten metal, said means comprising a piece of metal which is formed into a generally cylindrical structure for contraction and expansion when placed in a tube of such a device.

* * * * *

UNITED STATES PATENT AND TRADEMARK OFFICE
CERTIFICATE OF CORRECTION

PATENT NO. : 4,084,441
DATED : April 18, 1978
INVENTOR(S) : Robert F. McDevitt

It is certified that error appears in the above-identified patent and that said Letters Patent is hereby corrected as shown below:

On the title page, Item [73] Assignee:

"Charles S. Penfold, Fort Wayne, Ind." should be deleted.

Signed and Sealed this

Fifth Day of March 1985

[SEAL]

Attest:

DONALD J. QUIGG

Attesting Officer

Acting Commissioner of Patents and Trademarks